United States Patent [19]

Begemann et al.

[11] Patent Number: 5,978,709
[45] Date of Patent: Nov. 2, 1999

[54] PACEMAKER SYSTEM WITH IMPROVED TECHNIQUES FOR PREVENTING AND SUPPRESSING ATRIAL ARRHYTHMIAS

[75] Inventors: Malcolm J. S. Begemann, Velp; Johannes S. Van Der Veen; Xander Evers, both of Dieren, all of Netherlands

[73] Assignee: Vitatron Medical, B.V., Dieren, Netherlands

[21] Appl. No.: 09/098,162

[22] Filed: Jun. 16, 1998

[51] Int. Cl.⁶ ................................................... A61N 1/362
[52] U.S. Cl. ............................................................. 607/14
[58] Field of Search ...................................... 607/4, 9, 14

[56] References Cited

U.S. PATENT DOCUMENTS

| | | |
|---|---|---|
| 5,134,997 | 8/1992 | Bennett et al. . |
| 5,247,930 | 9/1993 | Begemann et al. . |
| 5,312,453 | 5/1994 | Shelton et al. . |
| 5,340,361 | 8/1994 | Sholder ........................................ 607/9 |
| 5,713,929 | 2/1998 | Hess et al. ................................. 607/14 |

*Primary Examiner*—William E. Kamm
*Assistant Examiner*—George R. Evanisko
*Attorney, Agent, or Firm*—Michael J. Jaro; Harold Patton

[57] ABSTRACT

There is provided a pacing system having special functions for treating the patient's atrium with atrial pacing so as to reduce the probability of occurrence of dangerous atrial arrhythmias. The pacemaker of the system provides for atrial Pace_Conditioning, whereby the patient's normal intrinsic atrial rate is overridden by higher rate pacing whenever a predetermined sequence of intrinsic heartbeats is sensed. The pacemaker also provides for special pacing routines following the detection of one or more PACs. The PAC response routines include pacing at an elevated rate for a predetermined time or number of beats, and smoothing out pacing intervals for one or several cycles following the occurrence of a PAC. The pacemaker also includes a post-exercise function, for overtaking the intrinsic rate and pacing the heart following exercise, the pacing being in accordance with a predetermined program which holds a relatively higher rate longer than normal post-exercise, so as to provide enhanced blood flow to the cardiac tissue and prevent the onset of ischemia.

10 Claims, 12 Drawing Sheets

PACEMAKER SYSTEM WITH IMPROVED TECHNIQUES FOR PREVENTING AND SUPPRESSING ATRIAL ARRHYTHMIAS

FIELD OF THE INVENTION

This invention lies in the field of cardiac pacemakers and, more particularly, pacemakers which provide pacing treatments designed to prevent or suppress dangerous atrial arrhythmias.

BACKGROUND OF THE INVENTION

An arrhythmia, as used herein, is described as a disturbance in the normal rate, rhythm or conduction of the heartbeat. More specifically, an atrial arrhythmia is such an arrhythmia which has its site of origin in the atria. An atrial tachycardia is a condition where the atria contract at a high rate, e.g., 100 or more beats per minutes. In paroxysmal (temporary) atrial tachycardia (PAT) an ectopic atrial focus becomes a pacemaker for the heart for the duration of the tachycardia. This duration may vary from seconds to several days. The irritable atrial focus that causes the atrial tachycardia normally causes ventricular tachycardia at the same frequency when AV conduction is normal. Another arrhythmia is termed "atrial flutter," in which situation a re-entry circuit in the atrial wall is the pacemaker of the heart, stimulating it with a frequency of approximately 200 to 300 beats per minute. In this situation, the AV node normally blocks every second, third or fourth impulse from the atrium and the ventricular frequency therefore varies from 60 to 50 bpm; the ventricular rate is regular when the block is constant, but irregular when the block varies.

In atrial fibrillation (AF), there is a chaotic and turbulent activation of atrial wall tissue. The number of depolarizations per minute exceeds 400 and the stimuli occur in the refractory period of the surrounding atrial myocardium. Under these conditions, the depolarization of the atrial wall is not coordinated, and a chaotic and non-effective activity controls the heart. With this irregular atrial activity, the AV node does not conduct every atrial stimulus, and the ventricles receive impulses in an irregular fashion.

Another form of atrial arrhythmia is the premature atrial contraction (PAC) or atrial extrasystole. The PAC is basically an atrial contraction which arrives early, before it is expected. While the sinus node is normally the pacemaker of the heart, when a PAC occurs a focus takes over the function of the sinus node for one beat. After such an ectopic atrial beat, the next beat from the sinus node is slightly delayed. Thus, the PAC causes an irregular cardiac rhythm. The irregularity may, in certain situations, be regular, as in Bigeminy or Trigeminy, i.e., one or two normal beats between each PAC. PACs may be a prelude to atrial tachycardia. As is known, tachyarrhythmias pose a danger of fibrillation, which in turn can be life threatening. Tachyarrhythmias are also associated with other low cardiac output symptoms, such as fatigue and syncope, and other undesirable manifestations. While many supra-ventricular tachyarrhythmias (SVT) are episodic, and marked by abrupt onset but also abrupt termination, they cause considerable patient distress and, if untreated, can lead to dangerous life-threatening conditions. The major danger of supra-ventricular tachyarrhythmias, especially chronic atrial fibrillation, is the development of blood clots which can cause stroke and possibly death.

In the patient where atrial tachycardia is the result of ectopic atrial focus in the pacemaker, one method of treatment is ablation the heart tissue where the focus is to be found. However, this is an expensive and dangerous procedure. Other techniques include anti-tachycardia, or cardioversion-type stimulation, where either a train of high rate pulses or one or more high energy pulses is delivered to the patient's heart in an attempt to restore a more normal rhythm. While these techniques can be valuable, and have achieved some success rate, it is clearly more desirable to treat a patient with an incipient atrial problem, to suppress it or to otherwise prevent the dangerous atrial arrhythmia from occurring in the first instance. Thus, it is known that incidences of PACs, if not treated, can develop into a more dangerous atrial arrhythmia, including tachycardia or fibrillation.

Another potential cause of atrial arrhythmia is ischemia, which is brought on due to restricted blood circulation to the cardiac tissue. When one performs exercise, the body can build up an oxygen debt or oxygen depletion. Under normal post-exercise circumstances, for a heathy patient, the cardiac rate remains high for a period of time, which ensures a sufficient blood flow to the heart. However, if the post-exercise rate drops too fast, this can result in ischemia. While the effect depends on the level of exercise and the duration of the exercise, for patients at risk of atrial tachycardia or fibrillation, there is a need to ensure that the cardiac rate does not decrease too rapidly after exercise episodes.

What is needed in the pacing art is a new therapy approach to provide pacing treatments which anticipate the causes of such dangerous atrial arrhythmias and which respond when needed to suppress the onset of such an arrhythmia. For example, there is a need for a pacing therapy designed to condition a patient's heart so as to provide stable consistent conduction pathways and refractory periods in the atrium, which can be achieved by stimulating the atrium from the same site and at stabilized rates. Similarly, the incidence of PACs can be reduced by increasing the heart rate when appropriate, e.g., by increasing the pacing rate to a stabilized higher rate following the occurrence of a PAC. Also, cardiac refractory dispersion can be reduced by providing a smooth transition from the PAC coupling interval to the underlying heart rate. Further, following patient exercise, the danger of ischemia and refractory dispersion can be reduced by taking over with pacing and limiting the decrease of pacing rate so that a higher than intrinsic rate is maintained for some period of time, thus providing a higher delivery of oxygen to the heart post-exercise.

SUMMARY OF THE INVENTION

In view of the above needs for treating patients who have a propensity for development of dangerous atrial tachycardia, there is provided a pacing system which includes a plurality of special pacing treatment features, termed AFP features. Each of these features can be programmed into the implantable pacemaker, and enabled by the treating physician upon detection of conditions that suggest that treatment is desirable. Alternately, the pacemaker may collect diagnostic information and automatically enable any one of the special treatment features.

A first AFP control feature of the pacemaker of this invention is a Pace_Conditioning feature, whereby the pacemaker overrides normal atrial senses and provides for pacing the patient at a rate above the underlying intrinsic rate for a great percentage of the time. In a preferred embodiment, upon sensing a physiological atrial beat, the pacing rate is raised by a predetermined step above the intrinsic rate, and decreased at a programmed rate of decrease back toward the lower rate limit until one or more additional intrinsic beats is detected, whereupon the higher conditioning pacing takes over again.

In another feature of this invention, a routine is provided for post-PAC suppression pacing, whereby following a sensed PAC, or a predetermined pattern of PACs, the pacing rate is elevated by a predetermined step, e.g., 15 ppm above the underlying intrinsic rate. The increased pacing rate is maintained over a predetermined pattern; preferably the increased rate is held for a predetermined number of delivered pacing pulses, and then permitted to decrease back toward the lower rate limit. The period of high rate pacing may be ended by sensing of a normal sinus rhythm, but the routine prevents additional steps on top of steps in the event that another PAC is detected during the higher rate PAC suppression pacing.

In yet another embodiment, pacing treatment is provided by a routine which responds to a sensed PAC by first attempting to track the PAC with a synchronous ventricular pace pulse, and then times one or more succeeding atrial pace pulses to smooth out the succeeding heartbeat intervals. In a preferred embodiment, in the next cycle after the PAC, pacing is carried out at a rate which is the average of the underlying intrinsic rate and the PAC rate (the rate corresponding to the interval from the last normal atrial beat to the PAC).

In yet another embodiment, the pacemaker provides post-exercise pacing, which is carried out at a higher than normal rate to provide a greater than normal blood flow to the heart following exercise, thereby reducing the chances of resulting ischemia. In the post-exercise embodiment, the pacemaker continually generates an AFP pacing rate which is calculated to take over and pace the patient's heart before there is a substantial decrease in pacing rate following the end of exercise. After the post-exercise pacing takes over, the pacing rate decreases more slowly than the normal rate would decrease, and the rate of decrease is limited so as to avoid excessively high pacing for too long, but to ensure pacing at a higher than normal rate as rate drifts back down toward the intrinsic rate.

DESCRIPTION OF THE PREFERRED EMBODIMENTS

Figure 1:
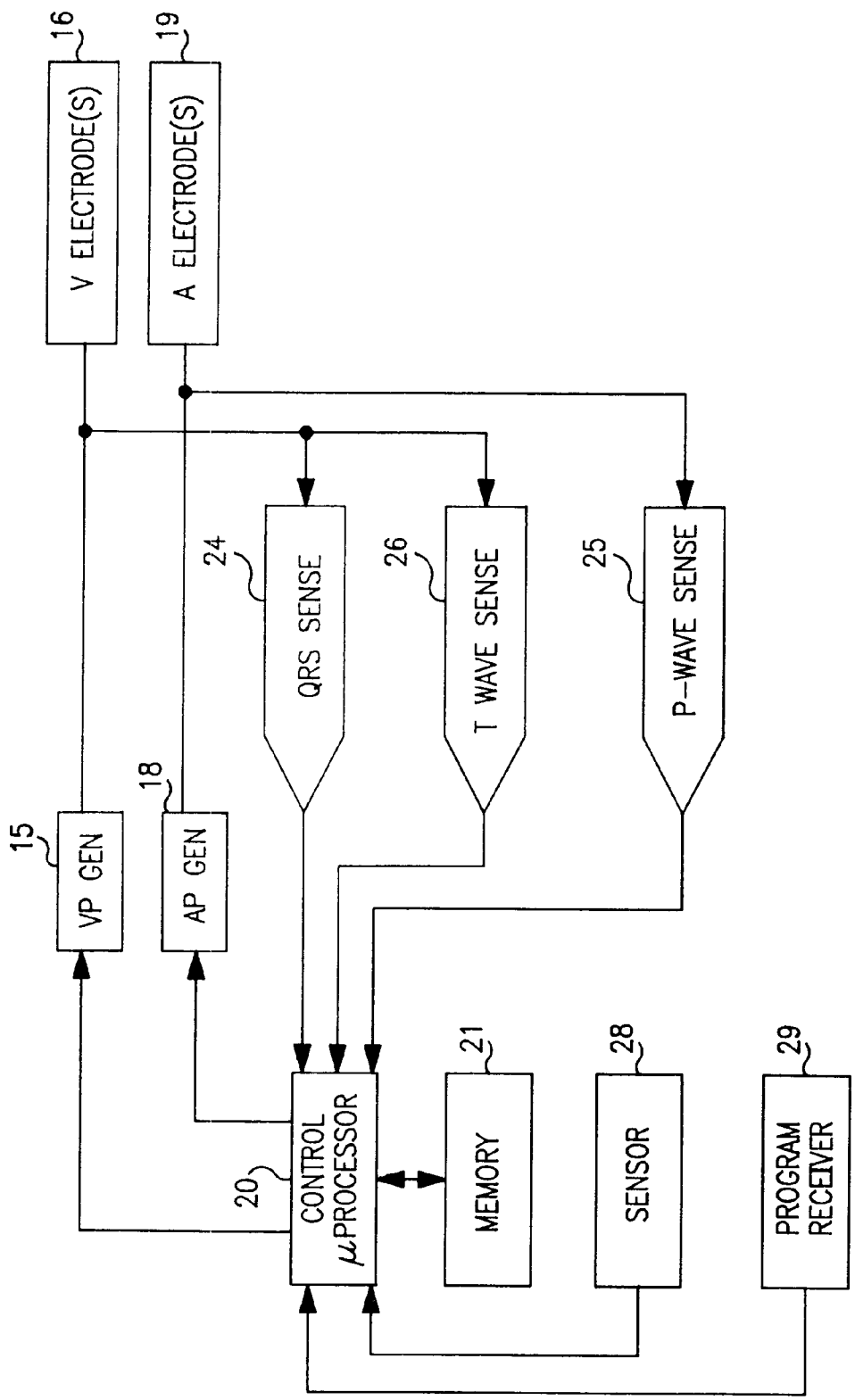
FIG. 1 is a block diagram of a pacing system in accordance with this invention, showing the primary functional components of such system.

Referring now to FIG. 1, there is shown a block diagram of the primary components of an illustrative pacemaker system which incorporates the features of this invention. A ventricular pace generator 15, controlled by control block 20, generates ventricular pacing pulses and delivers them to the ventricle through a lead which carries one or more ventricular electrodes 16. Likewise, atrial pacing pulses are generated by generator 18, also under control of block 20, which atrial pacing pulses are delivered through a lead to one or more atrial electrodes 19. Sensed QRS signals from the ventricular electrodes are processed at QRS sense block 24, and delivered to control block 20. Control block 20 suitably includes a microprocessor, and is interconnected with memory 21. Signals from the ventricular electrodes are also connected to T-wave sense block 26 for picking out T-waves and connecting them to block 20. The T-wave information is used, for example, in a QT rate responsive pacemaker. Similarly, P-waves picked up by the atrial electrodes are connected to P-wave sense block 25, which provides P-wave signal data to control block 20. A sensor 28, such as an activity sensor, may also be employed for a rate responsive pacemaker, providing an output which is connected to control block 20. Also, programmer receiver 29 may receive data and/or downloaded control software, which is connected to control block 20 and from there may be transferred to memory 21. Specifically, the patient's physician may program whether or not respective ones of the treatment routines of this invention are to be run. In the pacemaker system of this invention, the software for the illustrated routines is stored in appropriate RAM memory for use by the microprocessor in determining the atrial and ventricular escape intervals from cycle to cycle. The choice of the microprocessor and type and amount of memory is a matter of design choice. Such software control of pacemaker functions is well known in the art and within the skill of pacemaker designers.

Figure 2:
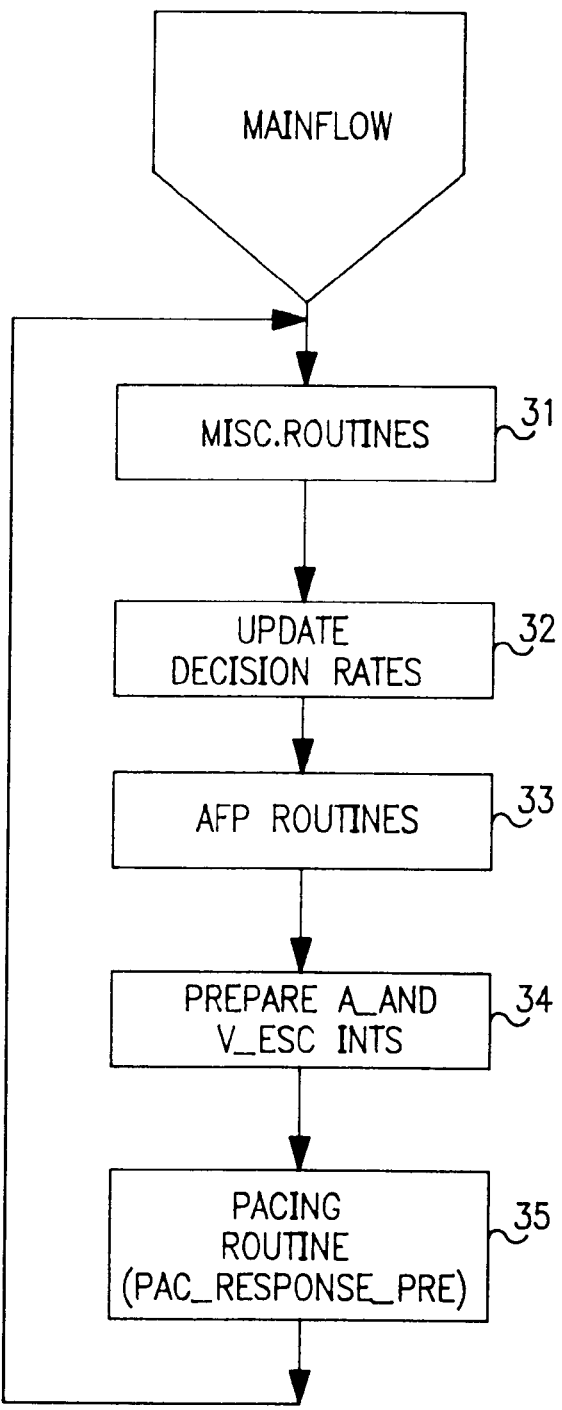
FIG. 2 is a flow chart showing the primary subroutines which are performed cyclically in support of the pacing treatments provided by this invention.

Referring now to FIG. 2, there is presented a flow chart of the main routines which are carried out cyclically as part of controlling pacemaker operation. It is to be noted that this flow chart is simplified in order to indicate the place of the primary routines required for the specific pacing treatments of this invention, and does not include any routines required for bookkeeping and other control purposes.

The main flow routine is entered at block 31, where the microprocessor carries out miscellaneous routines. Some of these routines are of a bookkeeping nature, not important to our explanation of this invention. Another function may be collection and analysis of diagnostic data, for decision-making. At 32, the pacemaker updates decision rates, e.g., dynamic pacing limit, dynamic tracing limit, and phys__rate. Reference is made to U.S. Pat. No. 5,247,930, which patent is incorporated herein by reference. The referenced patent contains a full discussion of decision rates. For present purposes, it is sufficient to note that phys_rate basically reflects the underlying intrinsic rate, or the atrial rate when pacing overtakes the intrinsic rate. As used hereafter, the term "underlying" rate may be the phys_rate or any measure of the current sinus rate. For practical reasons, any increase in phys_rate is limited to 2 ppm per beat. Also, it is to be noted that the dynamic pacing limit, or pacing rate, can be overridden by the sensor rate, if the pacemaker incorporates the rate responsive feature.

Following updating of decision rates at block 32, at 33 the pacemaker executes all but one of the special atrial fibrillation prevention (AFP) routines which are incorporated in accordance with this invention. As used herein, AFP refers to all the subject treatments for dealing with various dangerous atrial arrhythmias, or the onset of such arrhythmias. It is to be noted that these routines are run after the ventricular event, either a ventricular sense (VS) or a ventricular pace (VP). Next, at 34, the pacemaker prepares the atrial and ventricular escape intervals, and then goes to the normal pacing routine as indicated at 35. As discussed below, part of the pacing routine is to carry out a PAC_Response_Pre routine which is entered after the atrial event, as part of the pacing routine.

Figure 3:
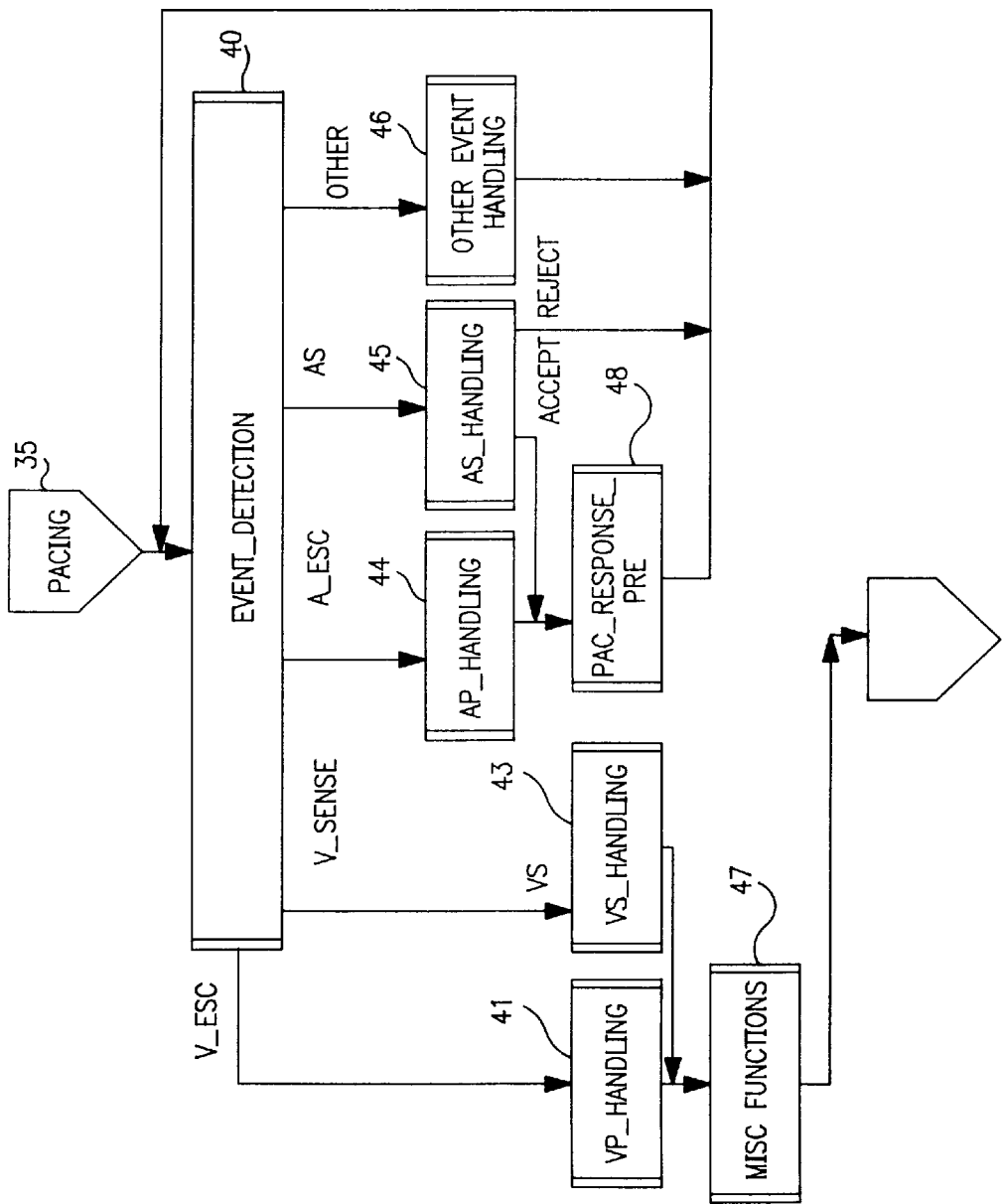
FIG. 3 is a flow chart showing the primary steps in handling different events as part of carrying out pacing in an exemplary pacemaker system embodiment of this invention.

Referring now to FIG. 3, there is shown a block diagram which illustrates the main logic steps taken in pacing routine 35. Subroutine 40, shown as "event-detection," is a routine for interpreting events and determining in what way the pacemaker is going to respond. A number of different events are indicated, and it is to be noted that other events may be included which are not shown in this flow diagram. If the ventricular escape interval (V_Esc) has timed out, the routine branches to 41, and prepares a VP for delivery. If there has been a VS, the routine goes to block 43 for handling. Then, at 47, the routine carries out miscellaneous functions such as updating the AV interval, and then exits. Note that the routine exits only after a ventricular event.

Returning to the event detection block 40, if the atrial escape interval (A_Esc) has timed out, the pacemaker goes to block 44 and handles the preparation and delivery of an atrial pulse (AP). After this, the pacemaker goes to block 48, and may execute the PAC_Response_Pre routine (if it is enabled) which is discussed in connection with FIG. 10A. Other functions may also be carried out at this time. Likewise, if an atrial sense (AS) is detected at block 40, the routine goes to subroutine 45 for AS handling. If the sensed atrial signal is accepted, the routine branches to block 48; if it is rejected, the routine returns to block 40. Also as shown, if other types of events are detected, the pacemaker goes to block 46 for specific handling. Such other events may include the detection of a T-wave, where T-waves are utilized; timeout of the refractory interval, etc. In response to such other events, the pacemaker returns to event detection at 40.

Figure 4:
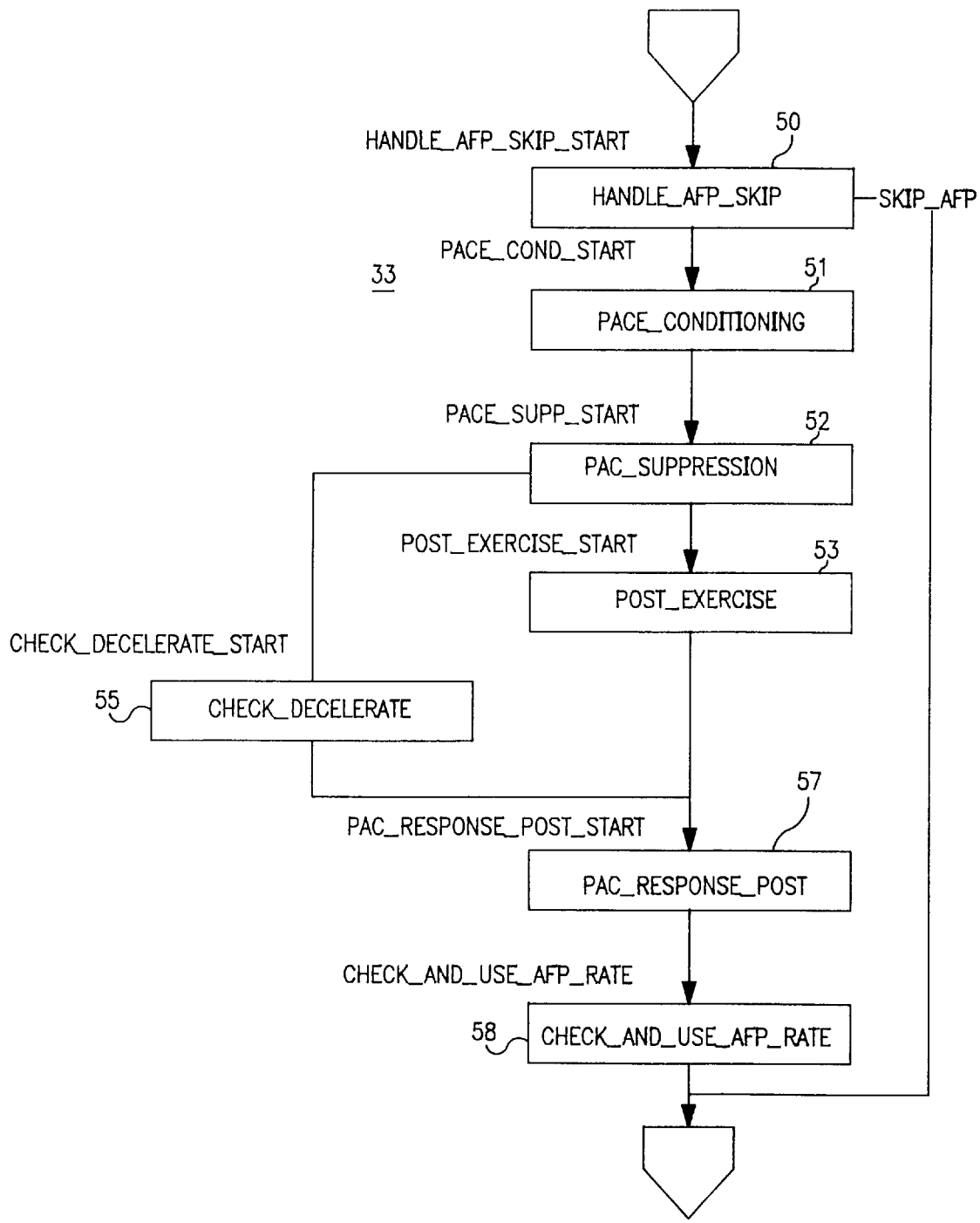
FIG. 4 is a flow diagram providing an overview of the representative routines for controlling pacing to provide prevention and treatment of atrial arrhythmias in accordance with this invention.

Referring now to FIG. 4, there is shown an overview flow diagram of a plurality of routines which provide for special pacing, either to prevent dangerous atrial arrhythmias or to respond quickly to a PAC. These routines are represented as respective blocks in FIG. 2, and are handled once a cycle after the last ventricular event. As indicated in the specific flow charts covering the four illustrative treatment routines, each such routine can be programmed on or off, i.e., the pacemaker can go through any selected ones or all of the routines that are available in the pacemaker. The routines are suitably programmed on or off by the physician, based on evaluation of data representing the patient's cardiac history and condition. Alternately, the pacemaker makes the decision automatically, based on accumulated event data (as acquired at block 31, FIG. 2).

Still referring to FIG. 4, at block 50 the pacemaker executes the Handle_AFP_Skip routine. This routine looks at different pacemaker conditions and determines whether the AFP routines should be entered. For example, the pacemaker checks to see if there is an End of Life (EOL) signal, and if so, stops execution of the AFP routines for the remaining lifetime of the pacemaker. Likewise, the routine checks to see whether the pacemaker is in a magnet mode or whether programming is active, in which it temporarily disables the AFP routines. If the AFP routines are not to be skipped, this Skip routine sets the Allow_Dec flag, which allows a controlled decrease in rate whenever one of the AFP routines determines that rate should be decreased.

Assuming that the AFP routines are not skipped, the first AFP routine that is entered and executed is the Pace_Conditioning routine 51. The principle of this routine is to condition the atrial activation pattern and refractory period by inducing atrial pacing in most cardiac cycles during a normal rhythm, e.g., in more than 95% of the cardiac cycles. As discussed in detail in connection with the Pace_Conditioning flow chart at FIG. 5, the routine regulates the pacing rate based on the underlying intrinsic rate, such that the pacing rate usually slightly exceeds the underlying intrinsic rate. Whenever spontaneous activity is sensed which is classified or interpreted as normal, the rate is increased by one predetermined step, e.g., 15 ppm, in order to obtain a paced rhythm. The rate is then subsequently decreased very slowly until either a next normal atrial beat is sensed or until the sensor rate or the lower rate limit (LRL) is reached. In order to prevent cumulative rate increases, following steps may be limited to a predetermined number of pulses per minute, e.g., 2 ppm. A step increase is not induced by a sensed PAC or a tachy beat, and is limited when a maximum pace conditioning rate is reached. Upon exiting this routine, an AFP_int, corresponding to an AFP rate, has been set, which will be used for preparing the atrial and ventricular escape intervals, as shown as block 34, FIG. 2, unless a higher AFP rate is set by one of the succeeding routines.

Still referring to FIG. 4, the pacemaker undertakes the PAC_suppression routine 52. The goal of this routine is to suppress the number of PACs by increasing the pacing rate. This routine may be indicated, for example, where somewhat regular PACs are observed. Whenever a PAC is sensed, the algorithm increases the rate by one step, e.g., 15 ppm. The rate is then stabilized for a certain period, e.g., 400–1,000 beats, after which the rate is decreased very slowly toward LRL. Such a stable period will be terminated and the rate decreased before the end of the period when a stable sinus rate (e.g., five consecutive normal atrial beats) or a tachycardia (e.g., five seconds of atrial tachy senses) is detected. Successive steps may be permitted. However, in order to prevent excessive rate increases, a second step increase (15 ppm with respect to the phys_rate) is preferably inhibited during the period of increased pacing rate until a stable intrinsic heart rate intervenes, thereby preventing an unwanted cumulative effect of rate increases. It is noted that the step up is preferably done with a fixed ppm value, e.g., 15 ppm relative to phys_rate, in order to eliminate an increased effect at high rates. If the algorithm of the PAC_suppression routine has been executed in response to a PAC, and the high rate pacing has not been completed, the pacemaker skips the post-exercise routine 53 and goes to the CHECK_DECELERATE routine 55, where it is determined whether the AFP rate is to be decreased.

The post-exercise routine 53 has the goal of limiting the speed of rate decrease following exercise by the patient, the limiting being dependent on the level and duration of exercise. The motivation of this routine is to track the phys_rate during exercise by adjusting the AFP rate sufficiently close to the phys_rate to prevent a significant rate drop following exercise; but at a great enough distance to minimize potential fusion beats. For example, a post-exercise (PE) target rate is continually adjusted to about 90% of phys_rate. If pacing takes over at the PE target rate, this rate is decreased only very slowly toward the lower rate limit, so as to accelerate elimination of the oxygen debt and prevent ischemia and refractory dispersion after exercise. Thus, the rate decay after exercise is programmable to be slower than the intrinsic drop-off in rate, and slower than the rate response sensor would otherwise indicate. The rate decay is made faster at high rates than at low rates, in order to reduce the risk that the rate might stay at inappropriate high rates for a long period of time, while increasing the percentage of pacing when at lower rates. This may be achieved by defining the rate decay in ppm per beat. Thus, a decrease of two ppm per 32 beats will result in a rate decrease of 20 ppm in 2–3 minutes when the average pacing rate is 120 ppm; and in 4–5 minutes when the average pacing rate is 70 ppm.

Routine 57 PAC_Response_Post, combines with PAC_Response_Pre routine 48 (FIG. 3) to eliminate post-PAC pauses and provide a smooth transition from the shortened PAC coupling interval to the underlying rate. The goal of this PAC response is to reduce refractory dispersion in the atrium by providing a smooth transition from the PAC coupling interval to the underlying heart rate. In the PAC_Response_Pre routine, the PAC is tracked when possible, with the AV delay prolonged by an AV delay extension in order to allow tracking of the PAC. If the PAC is not tracked, the atrial escape interval is modified to provide an atrial sync pace (ASP) at a controlled couple interval after the PAC, and also V_Esc is modified to obtain a correct AV delay between the ASP and the following VP. After the ventricular event, at routine 57, PACs (in the absence of an ASP) are followed by an atrial escape interval corresponding to a rate which is the average of the underlying rate as determined by the phys_rate, and the rate corresponding to the PAC coupling interval. The second beat after the PAC is delivered at a rate equal to the phys_rate.

Routine 58, titled Check_And_Use_AFP_Rate, determines whether the AFP rate is within a predetermined upper AFP limit (UAFPL) and the dynamic pacing limit (DPL). When the AFP rate is higher than the existing DPL, DPL is overwritten by the AFP rate, which is then used in defining escape intervals of the next beat (as performed at block 34, FIG. 2).

Figure 5:
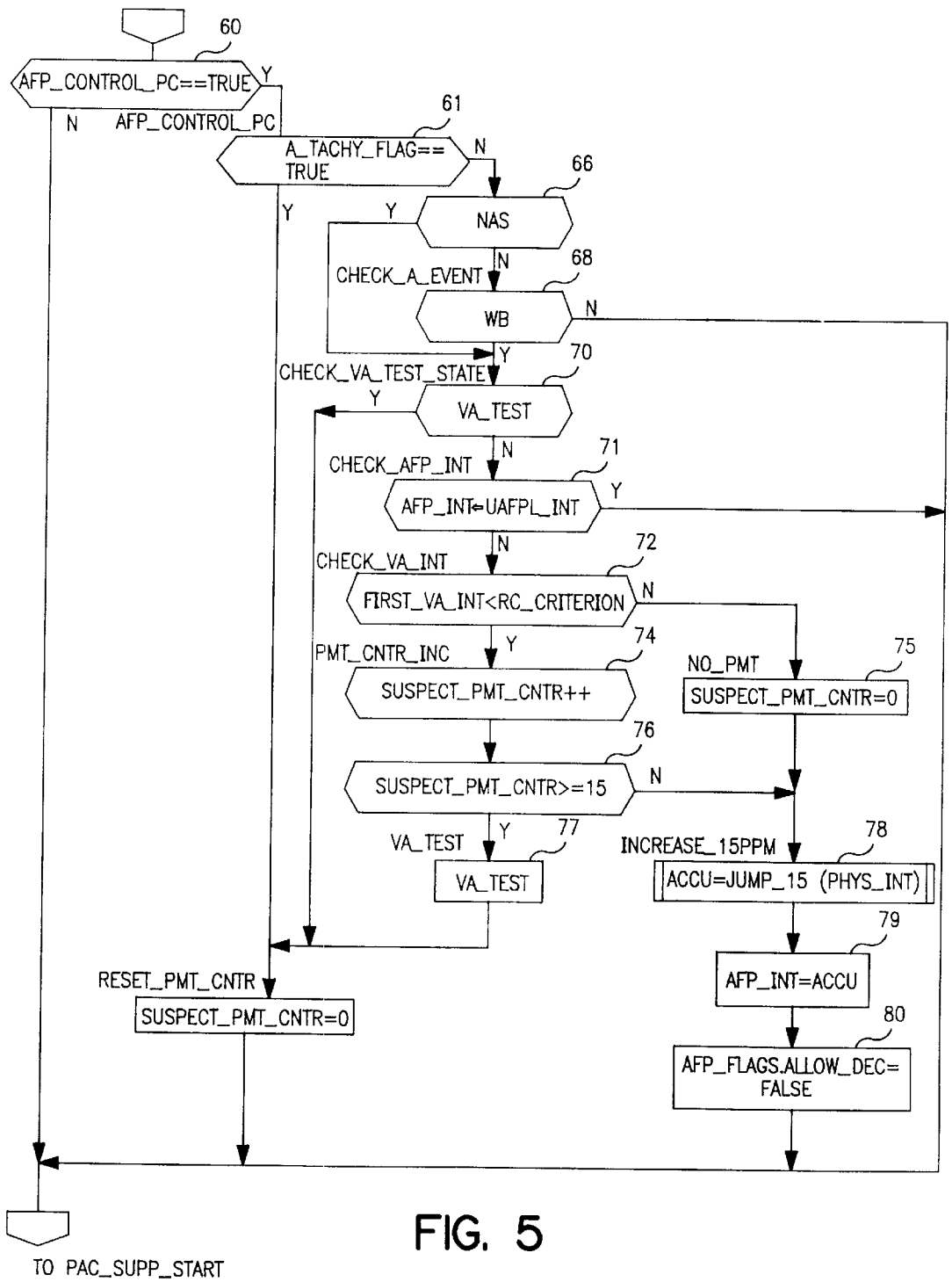
FIG. 5 is a detailed flow diagram of a pace conditioning routine in accordance with this invention.

Referring now to FIG. 5, there is shown a detailed flow diagram of a Pace_Conditioning (PC) routine, which is shown as block 51 in FIG. 4. At 60, the pacemaker determines whether the AFP_Control.PC flag is true, i.e., is the pacemaker programmed to execute this routine? If no, the routine exits directly to the PAC suppression routine 52. However, if the flag is set, the routine goes to block 61, and determines whether any of the atrial tachy flag is set true, meaning that there has been a first atrial tachy sense. If yes, the routine goes to block 65, and resets the suspect_PMT counter to zero.

Returning to 61, if the atrial tachy flag is not set true, the routine goes to 66 and determines whether the last atrial event was a normal atrial sense (NAS). If yes, the routine skips to block 70; if no, at 68 the pacemaker checks to determine whether the atrial sense is of a rate that falls in the Wenkebach (WB) window. If no, the routine exits, as a step increase is allowed only after a NAS or WB. However, if yes, the routine goes to block 70 to determine whether a VA test is ongoing (checking for PMT). If yes, the routine skips to block 65, but if no, it continues to 71 and determines whether the AFP interval is equal to or less than the UAFPL interval (corresponding to the programmed upper limit for AFP rate). If yes, meaning that the AFP rate is greater than the upper AFPL rate, the routine exits. If no, the routine goes to block 72 and checks the VA interval with respect to the retrograde conduction (RC) criterion. If the VA interval is less than the RC_criterion, pacemaker-mediated tachycardia is suspected, and the routine goes to block 74 and increments the suspect_PMT counter. At 76, it is determined whether this counter has reached a predetermined value, e.g., 15. If yes, at 77 a VA test is initiated, to detect whether there is PMT. If no, the routine branches to block 78. Reverting to block 72, if the VA interval does not suggest RC, the routine branches to 75 and sets the suspect_PMT counter to zero. At block 78, a subroutine titled "Jump_15" is initiated. The variable ACCU is set to provide an increase in pacing rate of 15 ppm relative to the phys_rate. This subroutine provides the interval that corresponds to a rate which is 15 ppm above the phys-rate. The total step is done preferably with a fixed ppm value in order to eliminate the effect of high rates, compared to programming the rates in ms. While a step of 15 ppm is suitable, it is to be noted that the step may be a design variable, e.g., it could be in a range of 10–20 ppm, subject to the upper rate limit. It is to be noted that there is a 2 ppm limitation on change of phys_rate per beat; consequently following a step, a next step can increase rate only 2 ppm per beat, thereby avoiding excessive cumulative increases in rate. This next increase is a design choice, e.g., it can be in the range of 1–3 ppm. At block 79, AFP_int is set to the ACCU variable, and at block 80 the Allow_Dec flag is set false, in order to prevent any decrease in pacing rate while the 15 ppm step is in progress.

It is to be noted that at the start of each cycle, the a Allow_Dec flag is set true in the AFP_skip routine. Consequently, whenever the PC routine is not stepping AFP rate upward, the Allow_Dec flag is true. After execution of the PC routine, the pacemaker goes to the PAC_suppression routine; if this routine does not control setting of the AFP rate, the pacemaker may go to the CHECK_DECELERATE routine 55, to decrease the AFP rate if the Allow_Dec flag has not been set false by the PC routine. The maximum Pace_Conditioning rate is suitably set equal to the maximum sensor rate for a rate responsive pacemaker, with a limit of 20 ppm below the upper tracking limit so as to avoid opening the Wenckebach window.

While the PC routine has been illustrated as providing a step rate increase in response to a single NAS, it is to be understood that the step increase can be conditioned on a pattern of ASs, e.g., 2–3 consecutive atrial senses, and is not limited to the specific embodiment of FIG. 5. Further, after the step increase, the higher rate may be maintained for a period, e.g., n beats. Thus, after the step increase, rate can be adjusted in accord with any predetermined program of rate adjustment, which may include holding the increased rate and then decreasing rate; alternately holding rate and decreasing; simply decreasing; etc.

Figure 6A:
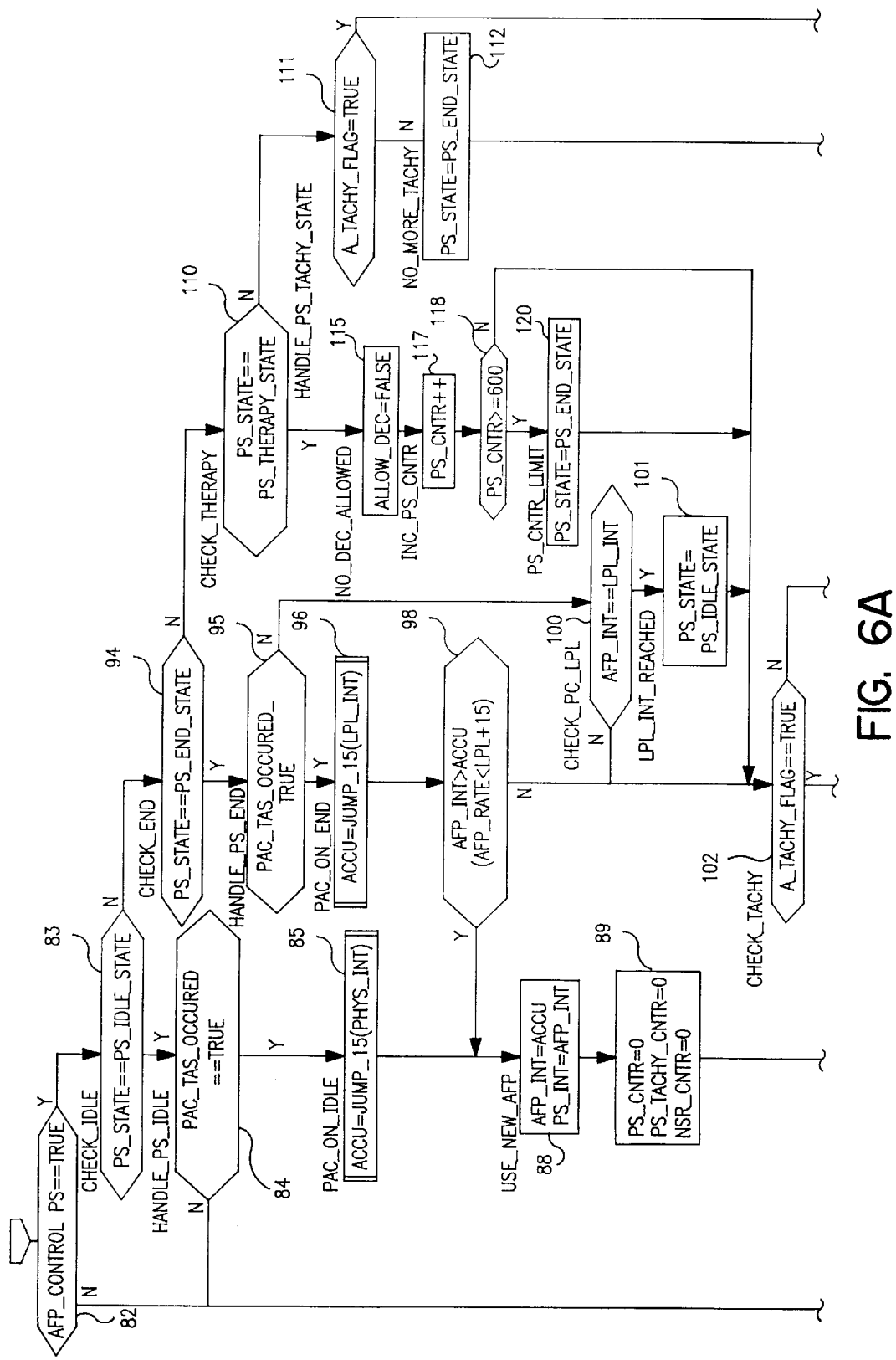
FIGS. 6A and 6B constitute a detailed flow diagram of a PAC suppression routine in accordance with this invention.
Figure 6B:
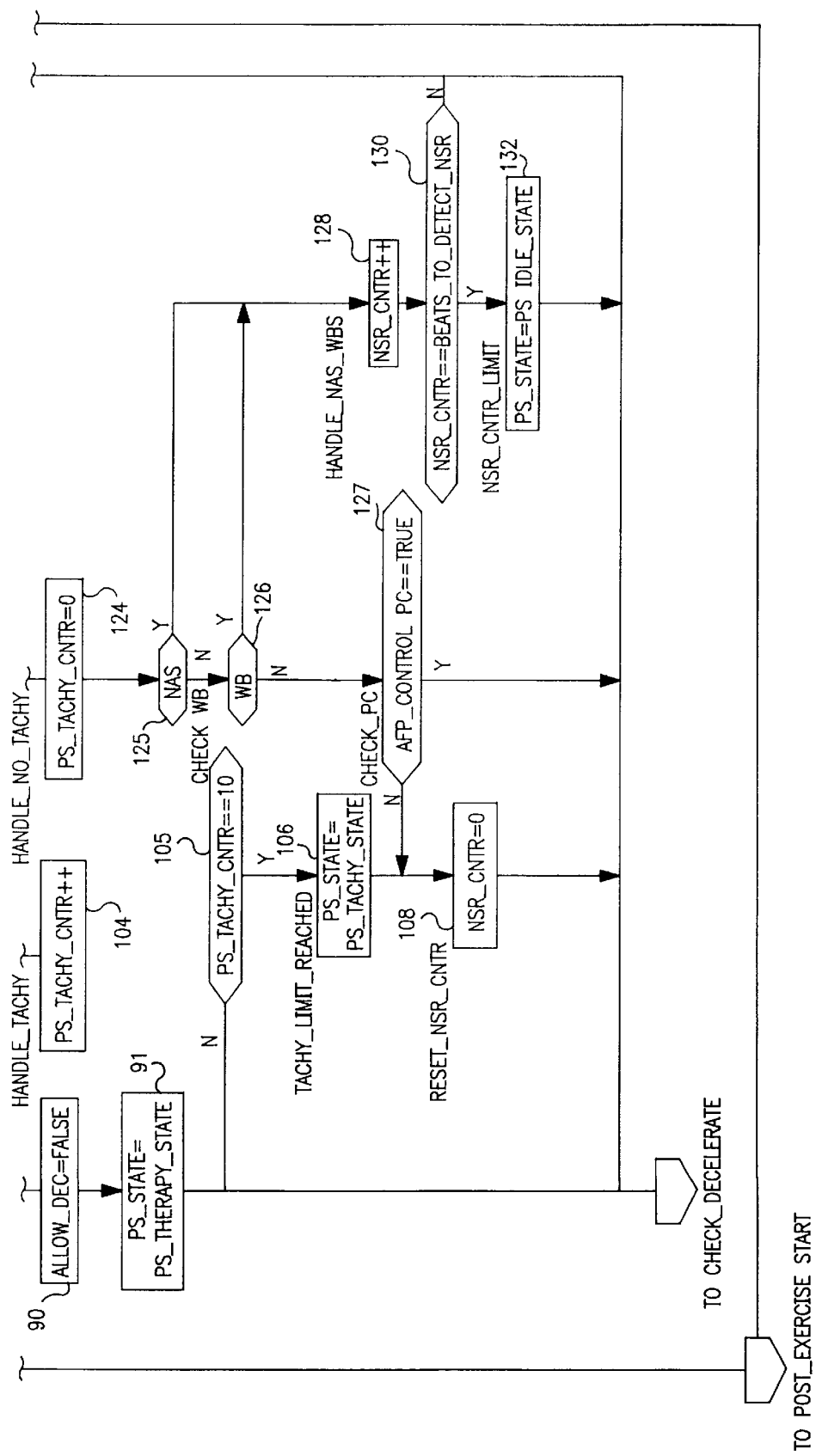

Reference is now made to FIGS. 6A, and 6B which constitutes a detailed flow diagram of the PAC_suppression routine, shown as block 52 of FIG. 4. It is the goal of this routine to reduce the incidence of PACs by increasing the pacing rate after a predetermined pattern of PACs; in a preferred embodiment, the pattern is the sensing of a single PAC. The basic method is to provide a step increase in pacing rate (AFP rate) after a PAC, or after the first tachy sense (TAS) not preceded by a PAC as determined by the pacemaker interpretation. The step increase is preferably a predetermined number of ppm with respect to the phys_rate, e.g., the rate is raised to 15 ppm above the phys_rate. The higher rate is continued for a predetermined period, e.g., 400–1,000 beats, but is terminated when five consecutive normal atrial beats (NAS) are sensed, or when three NAS are sensed with the pace conditioning routine running. The detection of return to a normal sinus rhythm may vary, e.g., 2–50 beats, or another programmed sequence involving normal atrial senses. Likewise, as seen in FIG. 6, the stable period of higher rate pacing is terminated when atrial tachycardia is sensed for a predetermined time, e.g., 5 seconds. Following this stable period, the rate is decreased at a decay rate which is defined in ppm per beat, e.g., 1–3 ppm per 24–40 beats.

Referring specifically to FIG. 6A, at 82 the routine checks to see if the PAC_suppression (PS) flag is TRUE. This may be set TRUE, for example, when the patient has experienced PACs with some regularity. If no, the pacemaker is not to run this routine, and it exits to the post-exercise routine. However, if the flag is set, the routine goes to 83 and determines whether the PS_state is IDLE. If idle, meaning that the algorithm has not been activated due to occurrence of a PAC, the routine branches to block 84 where it is determined whether a flag has been set to indicate a PAC or a first TAS. If no, the routine exits, but if yes, the routine proceeds to subroutine 85. Subroutine 85 carries out the jump-in pacing rate to 15 ppm above the phys_rate, defining a variable ACCU. Subroutine 85 determines the interval corresponding to the AFP rate which is 15 ppm above phys_rate. At 88, the AFP_int is set equal to the variable ACCU, overriding any AFP interval set by the Pace_Conditioning routine of FIG. 5. The PAC_suppression interval (PS_int) is set equal to the AFP_int. At 89, the PS counter, the PS tachy counter and the normal sinus rate (NSR) counters are set equal to zero. At 90, Allow_Dec flag is set false, prohibiting decrease in AFP rate. Following this, at 91, the PS_state flag is set to PS_THERAPY, and the routine exits to the CHECK_DECELERATE routine.

Returning to block 83 of FIG. 6A, if the PS state is not idle, the routine goes to 94 and checks to see if it is PS_END_state, meaning that the stable period has come to an end. If yes, the routine goes to block 95 and determines whether a flag has been set to indicate that another PAC or tachy sense has occurred. If yes, at 96 a jump routine is entered to define an ACCU variable which is 15 ppm above the lower pacing limit (LPL). At 98, it is determined whether the current AFP_rate is less than LPL+15. If yes, the routine branches to block 88, resetting the PS_int to correspond to LPL+15, following which the PS state is reset to the therapy state at block 91. If, at 98, the AFP rate is higher than LPL+15, the routine goes to block 102 to determine whether the atrial tachy flag is set, i.e., an atrial tachy arrhythmia is present. If yes, at 104 the PS_tachy counter is incremented, and at 105 it is determined whether this counter has reached a predetermined limit, e.g., 10. If no, tachy has not yet been confirmed and the routine exits to the decelerate subroutine. If at 105 the counter has reached the limit, tachy is confirmed and the PS_state is set equal to PS_TACHY as shown at 106. At 108, the NSR (normal sinus rate) counter is reset to zero.

Returning to block 94, then it proceeds to block 110 and determines whether it is in PS_THERAPY state. If no, the only state it can be in is the TACHY state, and the routine branches to 111 and determines whether the A_TACHY flag is set. If yes, the routine exits; if no, PS_State is set to BS_END_State at 112. Returning to 110, if the routine is in the THERAPY state, this means that it has jumped to a higher rate and is to be maintained for a predetermined number of pacing beats, absent the return of an intrinsic rhythm. The routine goes to 114 and determines whether the AFP_int is less than PS_int. If no, meaning that PS rate is higher than existing AFP rate, the routine goes to block 115 and sets the Allow_Dec flag to FALSE. Then, at 117 the PS counter is incremented, and at 118 the PS counter is compared to 600. If the PS counter has reached 600, meaning that the stable period has been completed, the routine goes to block 120 and sets the flag to PS_END_State; if the PS counter has not reached the predetermined limit, the routine skips block 120.

Retuning to block 102, if it is determined that the atrial tachy flag has not been set, the routine goes to block 124 and resets the PS_TACHY counter to zero. At 125, it is determined whether there has been a normal atrial sense. If no, at 126 the routine checks to see if an atrial sense in the Wenckebach window occurred. If no, the routine goes to 127 and determines whether the Pace_Conditioning routine is being run. If yes, the routine exits; if no, it goes to 108 and resets the NSR counter to zero. However, if at 125 or 126 it is determined that the answer is yes, the routine goes to block 128 and increments the NSR counter, i.e., counts atrial senses that come along at a normal sinus rate. At 130, it is determined whether the counter has reached the predetermined number of beats for detection of NSR, e.g., 5, and if yes, at 132 the state flag is set to IDLE, indicating end of the therapy. Note that if the Pace_Conditioning routine is not running, there must be five consecutive normal atrial senses detected in order to end the stable period. This is because the lack of an NAS or WBS results in the routine branching through 127 to 108, resetting the NSR counter to zero. There is thus provided a control routine for stepping pacing rate to a level above the normal atrial rate (phys_rate) whenever a normal atrial signal is sensed, and maintaining it there for a predetermined period, or until a normal sinus rhythm is detected. As long as the stable period is running, the Allow_Dec flag is set FALSE, so rate is not decreased. As soon as the stable period is over, the routine returns to the END state, and in the absence of another PAC or TAS, the Allow_Dec flag is set TRUE the next cycle, permitting subsequent decrease of pacing rate. Of course, whenever the intrinsic rhythm again rises above the pacing rate, the conditioning routine jumps right up again and carries through with another conditioning episode of pacing above the intrinsic rate.

Figure 7A:
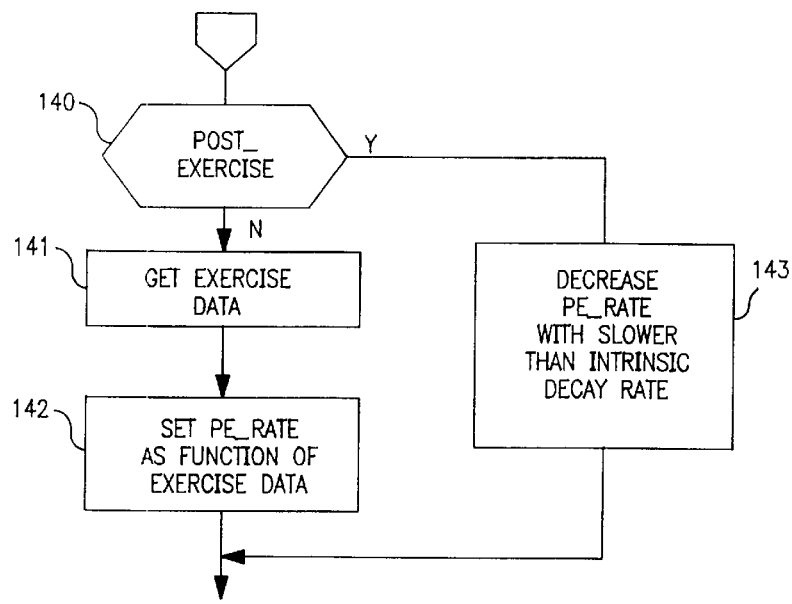
FIG. 7A is a generalized flow diagram showing a routine for post-exercise pacing in accordance with this invention.
Figure 7B:
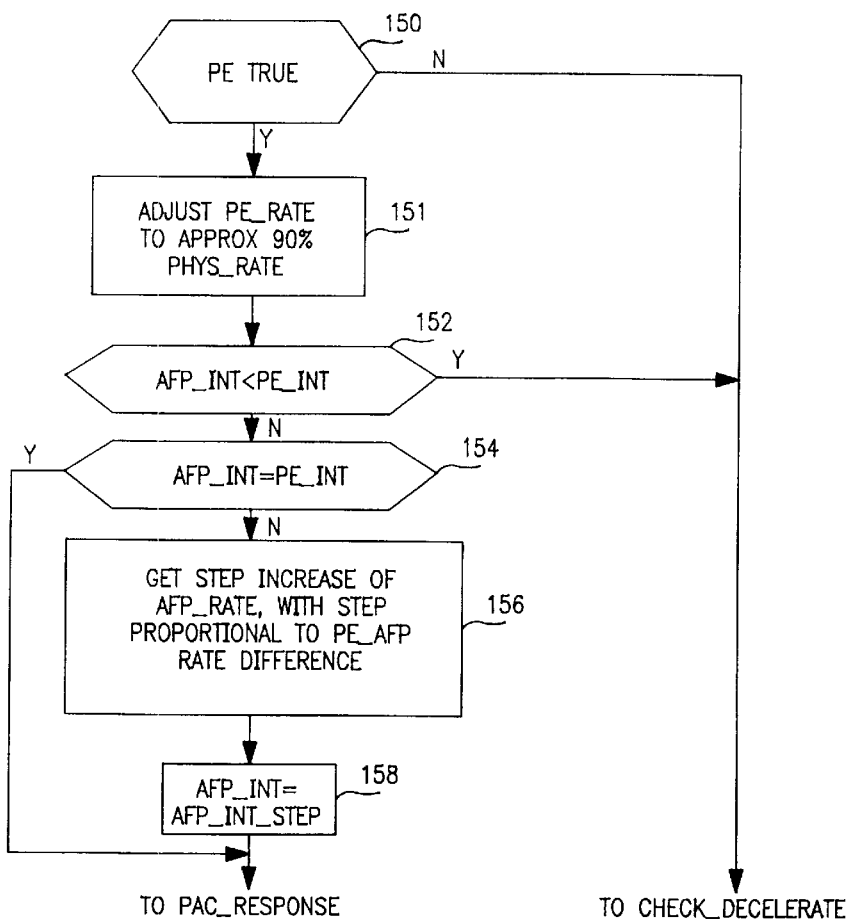
FIG. 7B is a detailed flow diagram of a specific embodiment of a post-exercise routine.
Figure 7C:
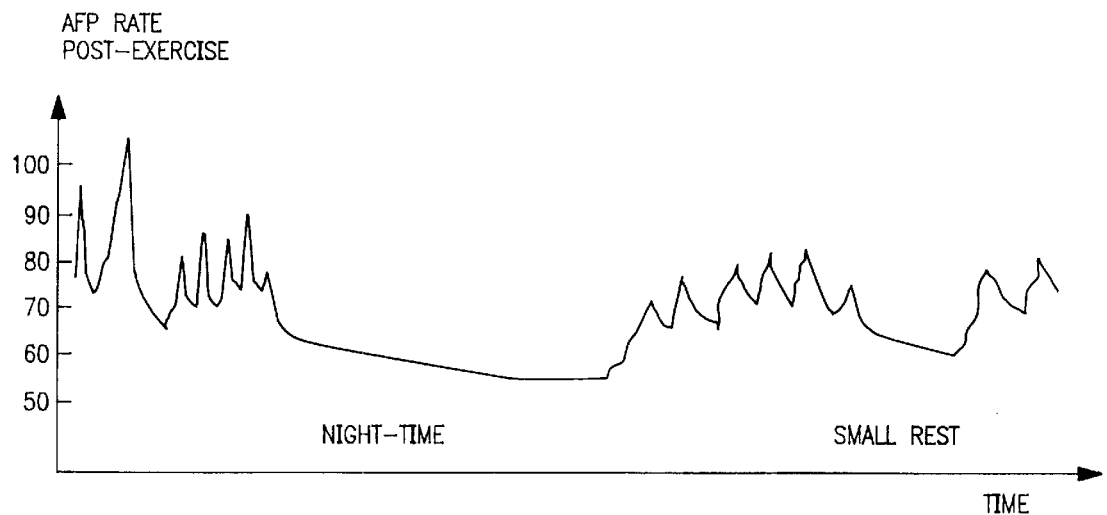
FIG. 7C is a time chart showing variation of the post-exercise rate, with a slow decay rate below about 70 ppm.

Referring now to FIGS. 7A–7C, there are illustrated generalized and specific embodiments of the post-exercise treatment in accordance with this invention. The general philosophy of the treatment is set forth in the flow diagram of FIG. 7A. At block 140, entered each cycle, the pacemaker determines whether the patient is post-exercise. As used herein, the term "post-exercise" means following a period of relative activity during which the patient's intrinsic rate, or sensor rate, is dropping. Thus, as seen in FIG. 7C, post-exercise may follow episodes of relatively vigorous physical activity, but may also occur during periods of relative rest after normal activity, such as night-time sleep, or small rest periods during the day. The manner of determining post-exercise preferably is based upon detection of a dropping intrinsic or sensor rate, or a combination of both.

If the patient is not post-exercise, then at 141 the pacemaker obtains exercise data reflective of the length and vigor of the exercise or activity. This data may be obtained from sensors, e.g., accumulating activity counts for a pacemaker having an activity-type sensor. Also, of course, the current sensor rate and/or intrinsic rate, and thus phys_rate, is also important to reflect the intensity or duration of exercise. At 142, the PE_rate, which is a target rate for pacing at the end of exercise, is determined as a function of the accumulated exercise data. As seen in the embodiment illustrated in FIG. 7B, the PE rate is suitably designed to continually move toward the phys_rate, e.g., move toward a given differential of ppm below the phys_rate.

Returning to 140, if the patient is post-exercise, the routine goes to 143 and decreases the PE rate with a slower than intrinsic decay rate. The object here is to maintain a higher A—A rate for some period of time following an exercise episode, so as to replenish the heart and prevent conditions which can lead to atrial tachycardia. The PE rate following exercise may be lowered at a constant decay rate, e.g., 1–3 ppm per 24–40 beats, or a more complex algorithm can be followed. An example of a more complex algorithm is a first decay rate whenever PE rate is above 90 ppm; a second slower decay rate when PE rate is below 90 but above 70 ppm; and a third even slower decay rate when PE rate is below 70 ppm. By making the decay rate very slow below 70 ppm, the post-exercise treatment can affect pacing behavior other than after exercise episodes. Thus, as seen in FIG. 7C, it can serve as diurnal rate control, providing an effective dynamic lower rate limit. For a patient with some moderate amount of exercise during the day, the PE_rate will not reach LRL. However, upon long periods of rest, e.g., sleep, the rate goes gradually down to LRL. By optimizing the decay to be very slow below 70 ppm, the effective LRL during daytime can be maintained between about 60 and 70 ppm, and go below this only at night or after a prolonged duration of rest.

Referring now to FIG. 7B, there is shown a more detailed flow diagram of a post-exercise routine, corresponding to block 53 of FIG. 4. If the PE routine is enabled, the PE flag is found TRUE at block 150. If no, the routine exits and goes to the CHECK_DECELERATE routine. For PE TRUE, at 151, the routine adjusts the PE rate to approximately 90% of phys_rate. Thus, PE is controlled to track the phys_rate and PE_int is adjusted each cycle to correspond to a rate which is 90% of phys_rate. At 152, PE_int is compared with the current AFP_int. If the PE_int is greater, meaning that the AFP_rate is higher than PE rate, the routine exits to CHECK_DECELERATE. If at 152 the answer is no, the routine goes to 154 and determines whether AFP_int is equal to PE_int. If yes, the routine exits to PAC_Response. If no, this means that the AFP rate is lower than the PE target rate, and should be increased. At 156, the routine generates a step increase of AFP_rate which is proportional to the difference of the PE rate minus the AFP rate. The step is generated in terms of ms, and at block 158 the step is subtracted from the current AFP_int to get the new AFP_int, corresponding to an increased AFP rate. For example, if the difference between the AFP rate and the PE rate is larger than a predetermined amount, AFP rate can be increased every 8 beats; if this difference is smaller, AFP rate is increased every 32 beats. In this way, the AFP rate is continually increased toward the target PE rate whenever it is detected to be lower than that rate, thereby continually tracking phys_rate. Note, of course, that whenever exercise ceases or diminishes, pacing takes over and phys_rate goes down with pacing rate. As a result, PE rate drops at block 151. This means that post-exercise, at 152 the routine will shortly branch to CHECK_DECELERATE, permitting the desired slow decrease in AFP_rate.

It is to be noted that in the embodiment of FIG. 7B, the effective decision of when the patient is post-exercise is made by the nature of the continuing adjustment of AFP rate toward PE rate, and the overtaking of the intrinsic rate by pacing. Note that by stepping the AFP rate toward the target PE rate proportionally to the difference, AFP rate reaches the target rate only with a relatively long and more vigorous period of exercise. For higher sinus rate, the pacing rate increases faster, and reaches a higher level than for lower sinus rates. Also, for longer lasting exercises, the pacing rate (AFP rate) is enabled to reach a higher value. By adjustment of the step increase of AFP rate, this rate can be enabled to reach 90% of phys_rate in approximately 5–10 minutes. Acceleration of the AFP rate by increase that are proportional to the rate difference provides an approximation of an exponential rate increase.

Figure 8:
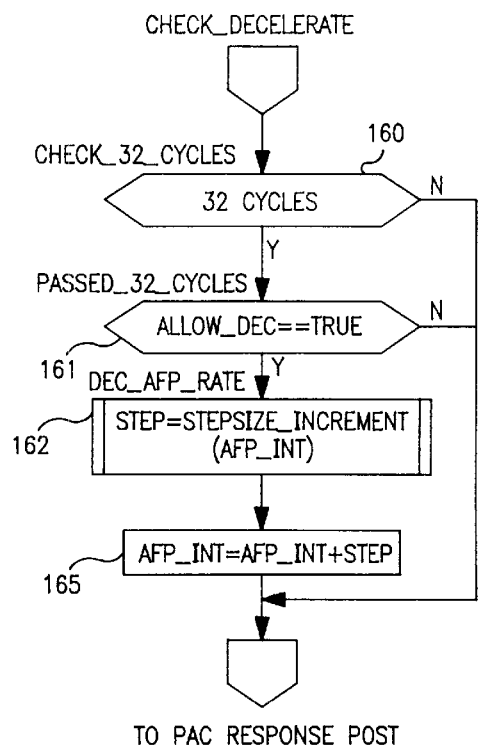
FIG. 8 is a detailed flow diagram of a routine for decreasing pacing rate when a rate decrease is called for by one of the pace conditioning, PAC suppression or post-exercise routines.

Referring now to FIG. 8, there is shown a flow diagram of the CHECK_DECELERATE routine. At 160, the counter is checked to determine whether 32 cycles have been passed. If no, the routine exits to the PAC_Response_Post routine, since AFP rate cannot be decreased. However, if 32 cycles have been passed, then at 161 it is determined whether the Allow_Dec flag is TRUE. If yes, at 162 the pacemaker carries out a subroutine for calculating a step, in ms, for incrementing the AFP_int. The step corresponds to a 2 ppm decrease in rate for the then current AFP rate. Following this, at block 165 AFP_int is incremented by the calculated step, thereby decreasing AFP rate by 2 ppm.

Figure 9:
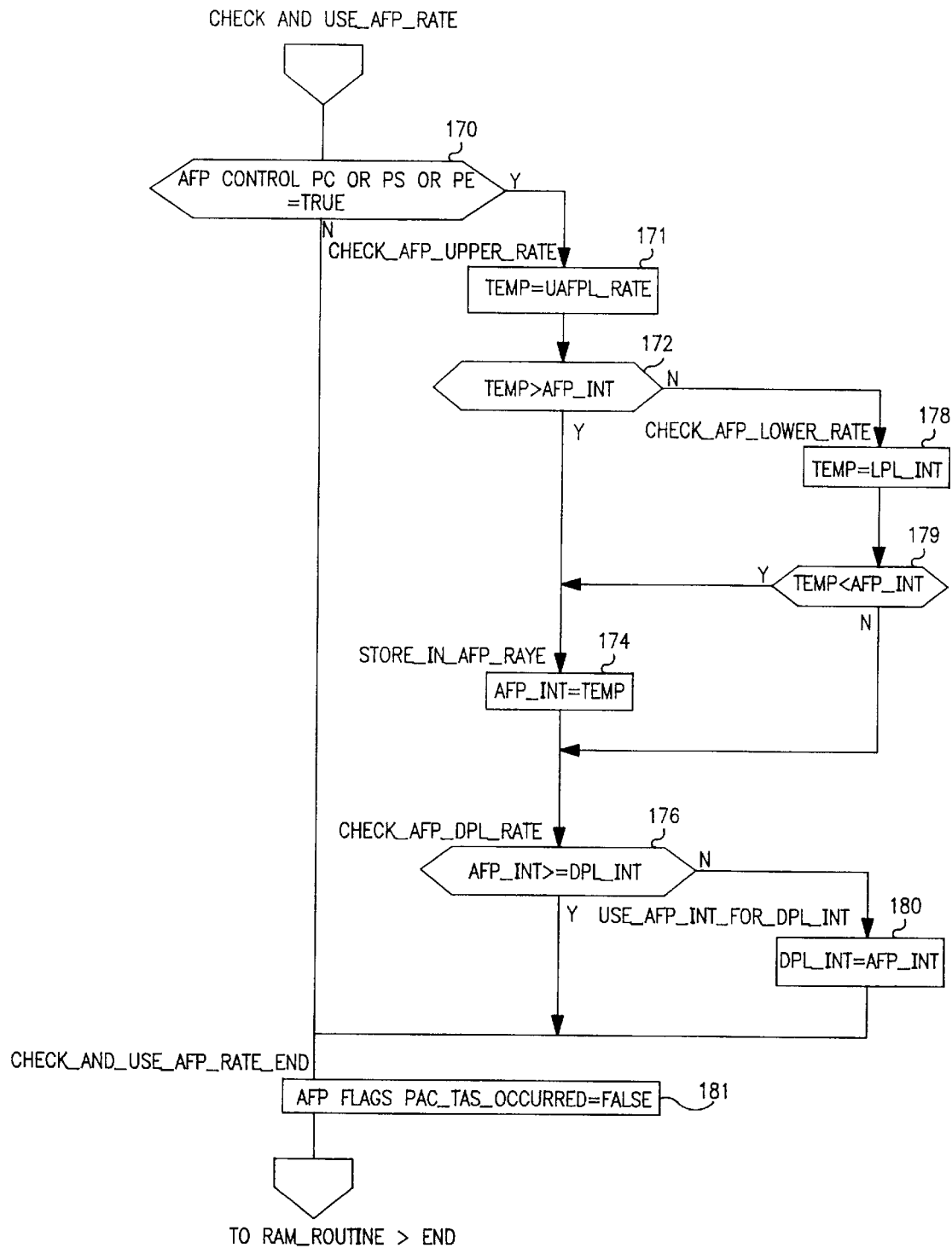
FIG. 9 is a flow diagram of a routine for determining whether the normal pacing rate is overridden by the AFP rate developed by one of the special routines for preventing atrial arrhythmias.

Referring now to FIG. 9, there is shown a flow diagram of the routine for using the applicable AFP rate that has been generated by one of the respective treatment routines. At 170, it is determined whether the PC, PS or PE routines is TRUE, i.e., is operative. If no, the routine goes to 181 and sets the various APF flags false. However, if one or more of the routines is running, at 171, the pacemaker obtains the interval corresponding to the upper limit of the AFP rate, i.e., UAFPL_int. At 172, this is compared to AFP_int, i.e., is UAFPL_int>AFP_int? If no, this means that the AFP rate is lower than the limit, and the routine branches to 178, 179 to check against the lower pacing limit (LPL). If, at 179 the AFP rate is found lower than LPL, the routine branches to block 174; if it is found higher, the AFP rate is in the usable range, and the routine branches to block 176. Note that at block 174, the AFP_int it set to correspond to either the high limit or the LPL limit. At 176, it is determined whether the AFP_int is greater than or equal to the DPL_int. If no, this means that the AFP rate is higher, and it overrides the DPL rate, and at block 180 the DPL_int is set equal to AFP_int. If the answer at 176 is yes, this means that the dynamic pacing rate is higher, and the routine exits. The value of DPL as determined at block 32 of FIG. 2 is used at block 34 to determine the escape intervals.

Figure 10A:
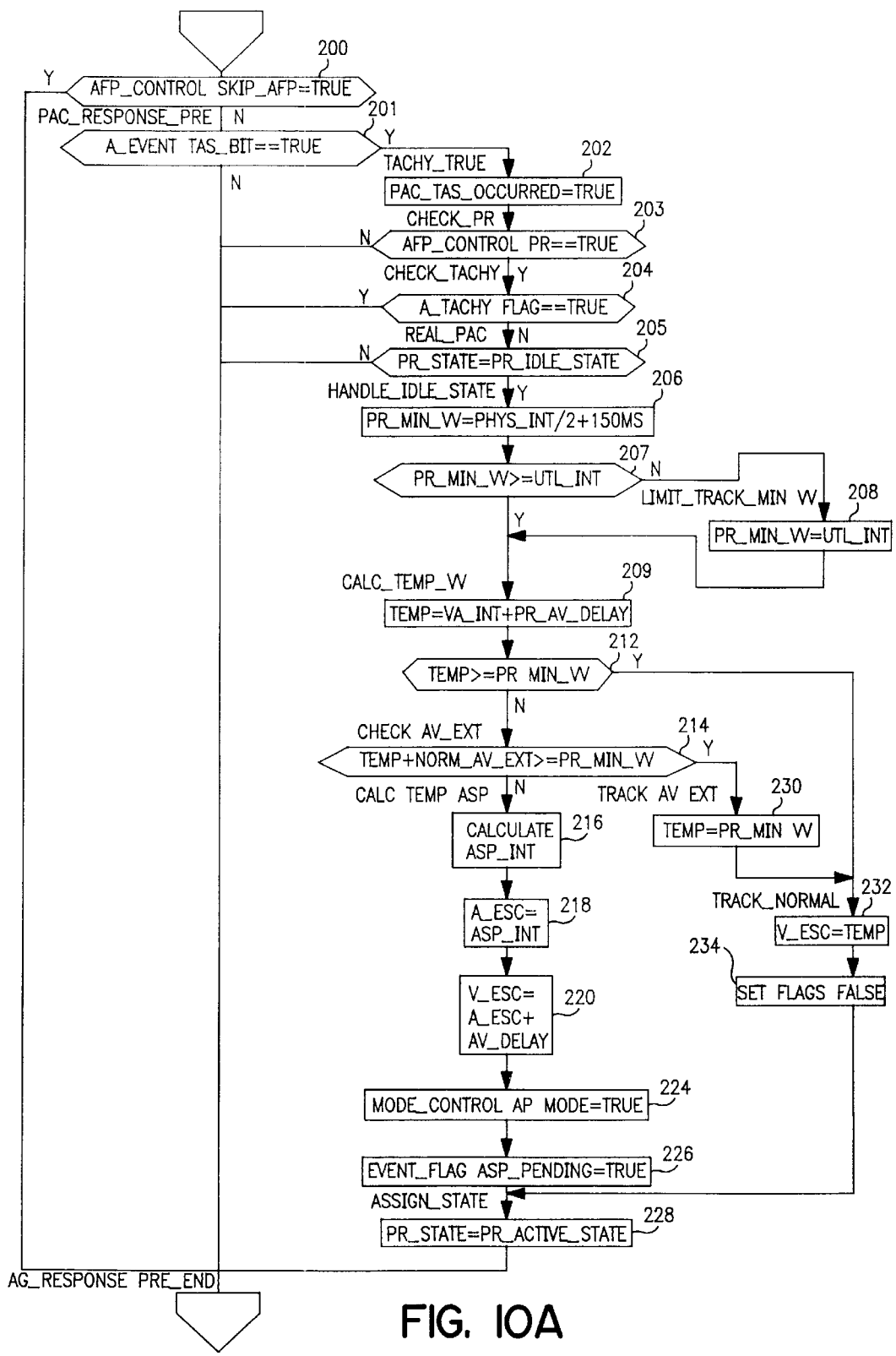
FIG. 10A is a flow diagram of a first PAC response routine run after a sensed PAC, to try to track the PAC or deliver a first atrial sync pulse.

Referring now to FIG. 10A, there is shown a routine which is run following AS handling, as seen at block 48 of FIG. 3. This routine is initiated by detection of a PAC, and has the objective of smoothing out the cardiac cycles following the premature beat. At 200, the pacemaker determines whether the AFP control should be skipped. If no, at 201 it is determined whether the TAS bit is true, meaning that there is a PAC or a tachy sense. If no, no response is in order, and the routine exits. However, if yes, the routine goes to 202 and sets a flag to indicate that a PAC or TAS has occurred. In 203, it is determined whether the PAC_Response routine is enabled. If yes, the routine proceeds to 204 and determines whether the atrial tachy flag is set TRUE, meaning that an atrial tachy episode has been identified. If yes, the routine exits. If no, this means there is a PAC, and the routine proceeds to 205 and determines whether the PAC-response routine is currently in the IDLE state. If yes, at 206 the routine establishes a minimum Vv interval, PR_min_VV, which is suitably calculated as phys_int/2+150 ms, approximately 30 ppm above phys_rate. Following this, at 207 this minimum Vv interval is compared to the upper tracking limit interval. If it is not greater, then at 208 the interval is set equal to UTL_int. At 209, a variable "temp" is set for the VV interval, being equal to VA_int+PR_AV_Delay. Then, at 212 it is determined whether this variable is greater than the previously determined minimum. If yes, the PAC can be tracked, and the routine goes to block 232 and sets the V_Escape interval to the Temp variable. At 234, certain flags are set FALSE, to be consistent with the tracking condition.

Returning to 212, if the W value is not long enough to maintain the minimum W interval, the routine goes to 214 to determine whether tracking can be done with an extension of the AV interval. If yes, the routine branches to 230 and sets the Temp variable to PR_min_W, since the full AV extension is not needed. Then at 232 the ventricular escape interval is set accordingly.

Returning to 214, if the determination is that the PAC cannot be tracked even with an AV extension, the pacemaker goes to block 216 and calculates an interval for delivery of an atrial sync pulse, ASP_int. ASP_int is suitably calculated to correspond to the average of the PAC rate and phys_rate. At 218, the atrial escape interval is set equal to ASP_int, and at 220 the ventricular escape interval is set equal to A_Esc+AV_Delay, so that the VP is delivered at an appropriate interval following the ASP. Following this, at 224 the mode control is set to the AP mode, and the ASP_Pending flag is set TRUE at 226, enabling delivery of the ASP. At 228, the PR_Active_State is set, meaning that a PAC has just been handled, which informs operation of the PAC Response_Post routine which is run after the ventricular event.

Figure 10B:
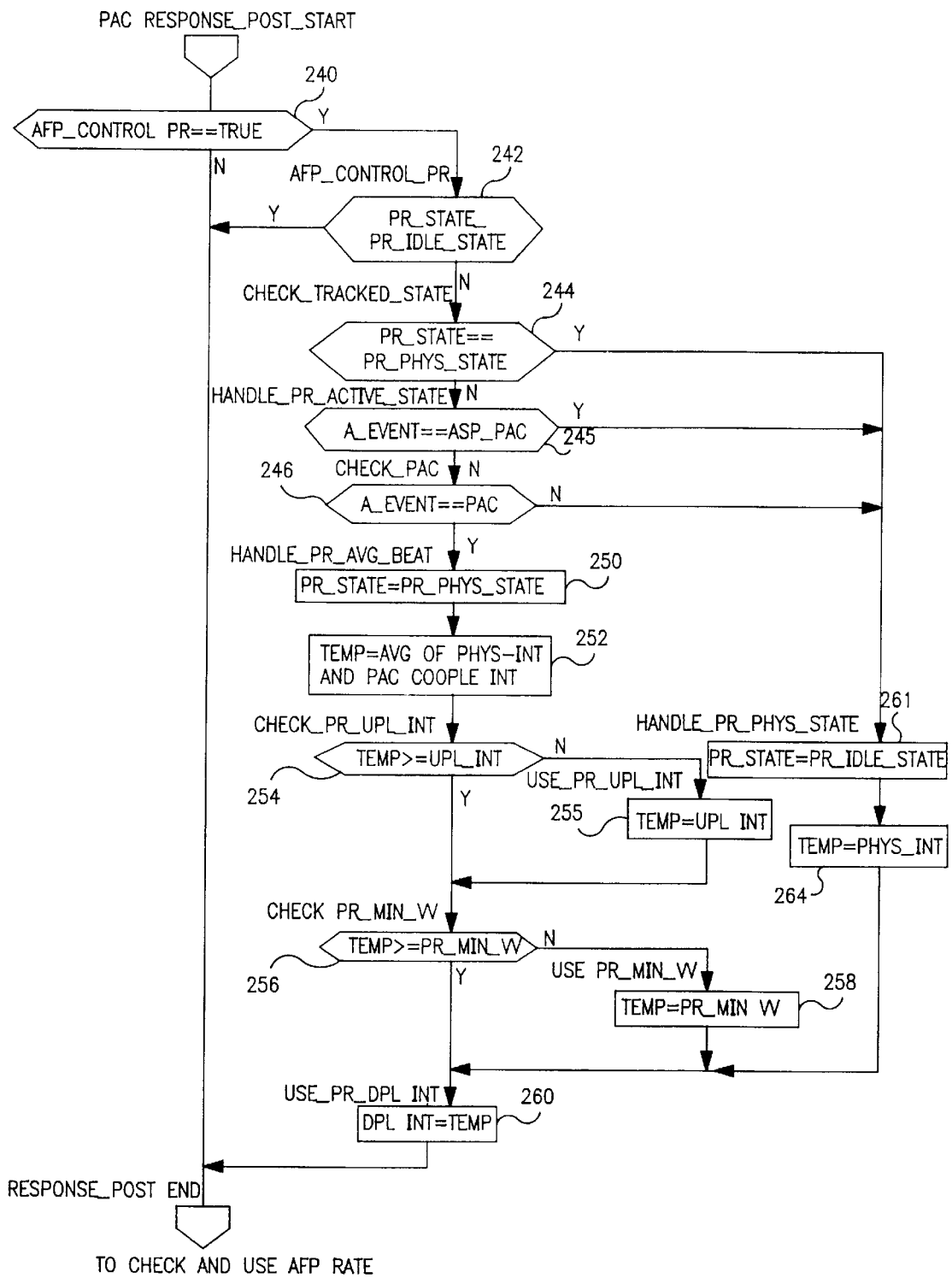
FIG. 10B is a flow diagram of a second PAC response routine which is run after the ventricular event to smooth out the cardiac rate.

Referring now to FIG. 10B, there is shown a detailed flow diagram of the PAC_Response_Post routine. The purpose of this routine is to space out the cardiac cycles following a PAC. Briefly, if the PAC has been tracked or followed by a VS, the first pacing beat after the PAC is delivered at a rate which is the average of the phys_rate and the PAC rate, while the second beat is delivered at the phys_rate. If the PAC was not tracked but an ASP was delivered following the PAC, then the following beat is delivered at the phys_rate.

At 240, the pacemaker checks to see if the PAC_Response flag is set TRUE. If yes, the routine proceeds to 242 and determines whether the PR_state is IDLE. If yes, this means that there has been no PAC to initiate the routine, and so it exits. However, if no, then the routine proceeds to 244 and checks to see whether it is in the PHYS state. If yes, this means that one post-PAC atrial pulse has been delivered, and the routine proceeds to 261 and places the PR_state in IDLE. Then, at 264, the variable Temp is set equal to phys_int. following this, at 260, the dynamic pacing limit interval is set equal to phys_int, whereby the second pace following the PAC is delivered at the phys rate.

Returning to 244, if the routine is not in the PHYS state, it must be in the ACTIVE state, and at 245 the pacemaker checks to see whether an ASP has just been delivered. If yes, the routine branches to 261, so that the pacing limit is set equal to the phys_rate. If at 245 it is determined that there has not been an ASP, then at 246 it is determined if there had been a PAC. If yes, at 250 the PR state is set to PR_PHYS, and at 252 the variable temp is set to correspond to the average of the phys_rate and the PAC_rate (where PAC_rate corresponds to the interval from the prior atrial event to the PAC). This interval is compared to UPL_int at 254. If it is not larger, meaning that the corresponding rate would be greater than the upper pacing limit, the routine goes to 255 and sets temp to the UPL_int. If the interval is greater than UPL_int, the routine goes to 256 and compares it to the minimum allowable VV interval. If this comparison is negative, then the variable is set to the PR_min_VV at 258, meaning then that the pacing limit is set equal to the minimum VV value at 260. However, if the comparison is positive, then the average interval obtained at 252 is utilized at 260 as the pacing interval, so that the first beat following the PAC has an interval corresponding to the average of the phys_rate and the PAC rate.

We claim:

1. A rate adjustable pacing system, comprising:
   generator means for generating and delivering pacing pulses to a patient's heart;
   sensing means for sensing patient intrinsic atrial beats;
   rate control means for controlling the pacing rate of delivery of said pacing pulses;
   first means enabled upon occurrence of at least one of said sensed intrinsic atrial beats for increasing said pacing rate to a conditioning rate greater than said intrinsic rate by a predetermined number of pulses per minute;
   said first means further comprising limit means for limiting said conditioning rate to a predetermined maximum rate;
   second means enabled after said pacing rate is increased to said conditioning rate for decreasing said conditioning rate by a predetermined number of pulses per minute per delivered pacing pulse; and
   sync means for synchronously tracking sensed intrinsic atrial beats that occur at rates up to a predetermined upper tracking rate, and tracking limit means for limiting said conditioning rate to 15 to 25 pulses per minute below said upper tracking rate.

2. The pacing system as described in claim 1, wherein said first means further comprises step means for stepping up said pacing rate to a said conditioning rate which is 10 to 20 ppm above said intrinsic rate.

3. The system as described in claim 1, wherein said second means comprises means for maintaining pacing rate for a predetermined period, and then decreasing pacing rate.

4. The system as described in claim 1, further comprising programming means for enabling the operation of said first means and said second means.

5. The system as described in claim 4, further comprising means for interpreting whether sensed intrinsic atrial beats are premature atrial contractions and prevent means for preventing increase of pacing rate in response to a said premature atrial contraction.

6. A pacing system for pacing a patient's heart comprising:
   pulse means for generating and delivering pacing pulses to said heart at a controllable pacing rate;
   sensing means for sensing intrinsic atrial signals from said heart;
   rate means for determining the intrinsic rate of said sensed signals;
   control means for controlling said pulse means to generate and deliver pacing pulses to at least one of the patient's atria following sensing of an intrinsic atrial beat, said control means having increase means for increasing said pacing rate to a conditioning rate which is greater than said intrinsic atrial rate; and limit means for limiting any further pacing rate increase when an intrinsic atrial signal is sensed while said pacing rate is at said conditioning rate, wherein said limit means comprises means for increasing pacing rate by a predetermined pulses per minute smaller than the increase used to increase to the conditioning rate when an intrinsic atrial signal is sensed and said pacing rate is at said conditioning rate.

7. The system as described in claim 6, wherein said increase means comprises step means for stepping said pacing rate to a conditioning rate a predetermined number of pulses per minute above said intrinsic rate.

8. The system as described in claim 6, further comprising decrease means for decreasing pacing rate from said conditioning rate in the absence of a sensed intrinsic atrial signal.

9. The system as described in claim 6, wherein said limit means comprises means for determining a phys rate which is a function of said intrinsic rate, increment means for limiting the increase in said phys rate to a predetermined increment per sensed intrinsic atrial beat, and wherein said increase means comprises step means for stepping said pacing rate to a conditioning rate which is a predetermined number of pulses per minute above said phys rate.

10. The system as described in claim 6, wherein the predetermined pulses per minute is two.

* * * * *